US00PP37648P2

(12) United States Plant Patent
Hansen

(10) Patent No.: US PP37,648 P2
(45) Date of Patent: Aug. 25, 2026

(54) ***BAPTISIA* PLANT NAMED 'Musical Duet'**

(50) Latin Name: ***Baptisia* hybrid**
Varietal Denomination: Musical Duet

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 19/729,003

(22) Filed: Jan. 14, 2026

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson

(57) ABSTRACT

A new and distinct plant cultivar of hardy herbaceous *Baptisia* plant named 'Musical Duet' is characterized by flowers that are violet with a near-white keel beginning in late May and continuing for two to three weeks. The new plant has a narrow, medium height, upright, vase-shaped, multi-stemmed, winter-hardy habit with glaucous dark-green tri-foliate foliage and is suitable for landscaping as a specimen or en masse.

2 Drawing Sheets

Botanical classification: *Baptisia* hybrid.
Cultivar designation: 'Musical Duet'.

STATEMENT REGARDING PRIOR DISCLOSURES UNDER 37 CFR 1.77(B)(6)

*Baptisia* 'Musical Duet' was first promoted with a brief description and photographs on a website operated by Walters Gardens, Inc. on Feb. 1, 2025, followed by the "Walters Gardens 2025-2026 Catalog" initially distributed by Walters Gardens, Inc. on Jun. 4, 2025. Walters Gardens, Inc. obtained the new plant and all information about the new plant from the inventor. No plants of *Baptisia* 'Musical Duet' have been sold or offered for sale, in this country or anywhere in the world, nor has any disclosure of the new plant been made, more than one year prior the filing date of this application, and such sale or disclosure within one year was either derived directly or indirectly from the inventor and would therefore be a 35 U.S.C. § 102(b) exception.

BACKGROUND OF THE INVENTION

The present invention relates to a new and distinct cultivar of hybrid *Baptisia* plant, botanically known as *Baptisia* 'Musical Duet', and will be referred to hereafter by its cultivar name, 'Musical Duet', and the new plant. The new plant represents a new false indigo, a hardy herbaceous perennial grown for landscape and cut flower use.

'Musical Duet' arose from an ongoing breeding program of the inventor at a wholesale perennial nursery in Zeeland, Michigan with the specific intention of improving garden worthiness of perennial false indigo plants with a wider variety of flower colors and improved garden habit.

*Baptisia* 'Musical Duet' was a single seedling selection from an insect pollination of the unnamed, proprietary hybrid known only as H9-22-1 at the same nursery in Zeeland, Michigan in May of 2015. The seeds were then sown at the same nursery in Zeeland, Michigan in the February of 2016. The initial selection was made in the spring of 2017 at the same nursery in Zeeland and later given the breeder code 15-1-2.

'Musical Duet' was initially asexually propagated by stem cuttings at a wholesale perennial nursery in Zeeland, Michigan in 2020. The resultant plants have demonstrated that the new plant has remained stable and true to type in successive generations of asexual propagation.

The nearest comparison plants known to the inventor are: 'Grape Escape' U.S. Plant Pat. No. 36,083, 'Grape Taffy' U.S. Plant Pat. No. 26,587, 'Pink Lemonade' U.S. Plant Pat. No. 30,669, and 'Pink Truffles' U.S. Plant Pat. No. 26,588.

'Grape Escape' has a slightly taller habit, and the flowers have cream-colored keels and purple banners. 'Grape Taffy' is much shorter and more compact in habit and the flowers are reddish-purple with a buff-yellow keel. 'Pink Lemonade' has a taller habit and the flowers are dusty raspberry-purple with a pale-yellow keel. 'Pink Truffles' is significantly taller and broader in habit with soft pink flowers having a yellow keel.

The parent has bluish-purple flowers with a light yellow keel.

The new plant differs from all *Baptisia* known to the inventor in the following combined traits:

1. Flowers are violet with a near-white keel;
2. Flowering begins mid-May in Michigan and continues for about two to three weeks;
3. Narrow, medium-height, upright, vase-shaped, multi-stemmed, winter-hardy habit;
4. Glaucous, dark-green, tri-foliate foliage.

BRIEF DESCRIPTION OF THE DRAWINGS

The photographs of 'Musical Duet' demonstrate the unique traits of the new plant and the overall appearance. The colors are as accurate as reasonably possible with color reproductions. Variation in ambient light spectrum, source and direction may cause the appearance of minor variation in color. The accompanying photograph is of a six-year-old plant growing in an open full-sun trial garden in Zeeland, Michigan.

DETAILED BOTANICAL DESCRIPTION OF THE PLANT

Figure 1:
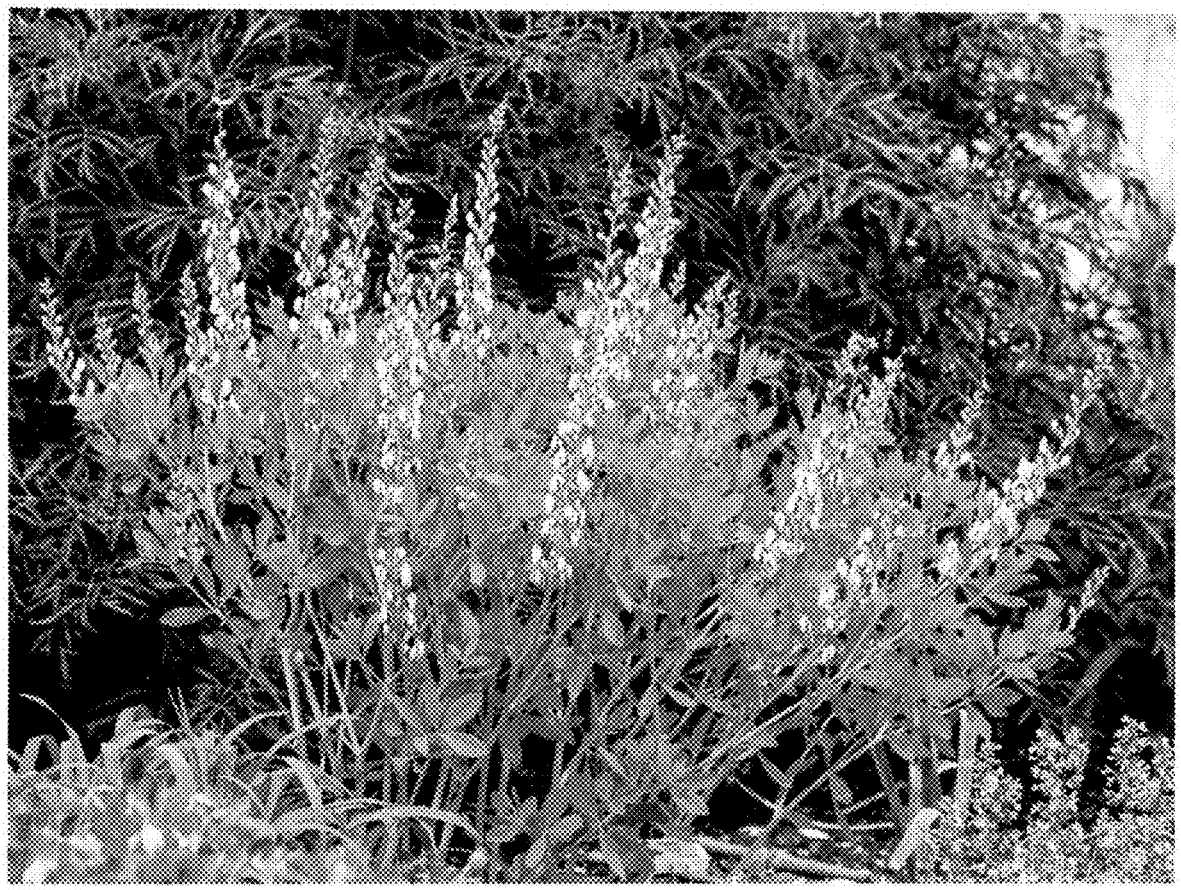
FIG. 1 shows the habit of a plant in full flower.
Figure 2:
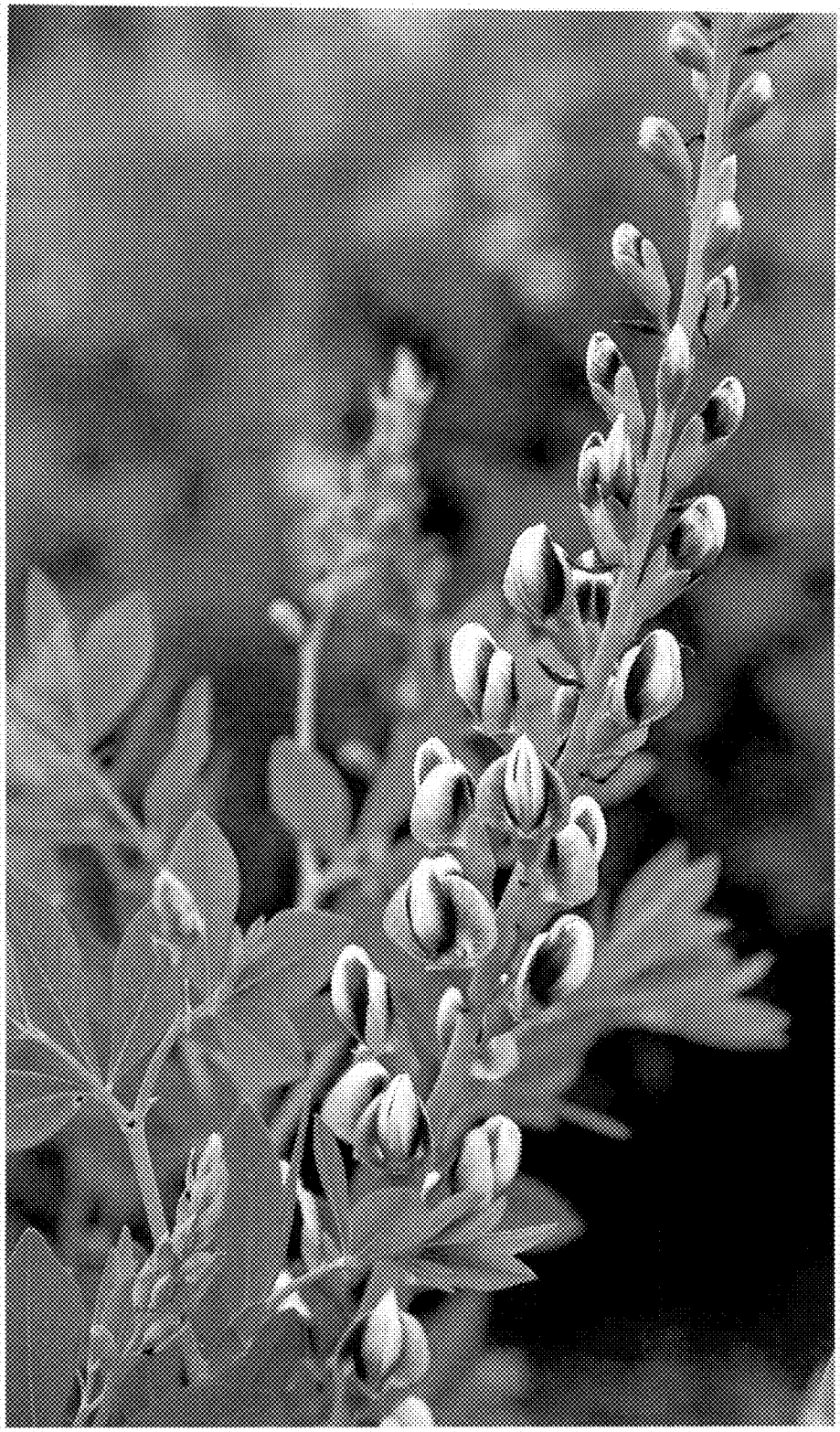
FIG. 2 shows a close-up of the inflorescence.

The following is a detailed description of a six-year-old plant of 'Musical Duet' as grown outdoors in a display garden at a wholesale perennial nursery in Zeeland, Michigan. Plants of the new cultivar have not been tested under all possible conditions. The phenotype may vary with changes in the environment, climate, and cultural conditions without any change, however, in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage;

Plant size: Stems and crown about 35 cm across at soil level, at flowering about 120 cm tall from soil to top of flowers and 130 cm wide just below initial flowers; at maturity plant foliage height about 127 cm tall and about 160 cm wide;

Roots: Fibrous, well-branched, long, deeply rooted;

Root color: Nearest RHS 161D;

Propagation method: Stem cuttings, rooting in about three weeks;

Growth rate: Moderate to average;

Stems: Rigid and upright; glabrous; highly glaucous; cylindrical with shallow longitudinal furrows; lower two to three nodes without leaves or branches; normally two to three branches per plant below terminal flower spike; about 36 stems per clump;

Stem size: Main stem to about 11 mm diameter at base and 107 cm tall, average about 98 cm long and about 9 mm diameter; to about 53 cm long from soil to below initial flowers;

Stem branches: Primary branches at 45 to 60-degree angle above horizontal, up to 52 cm long and 7 mm diameter at base, average for primary branches about 39 cm long and 5 mm diameter, smaller distally; and two to three alternate secondary branches per stem of about 22 cm long and 3 mm diameter, averaging about 14 cm long and 3 mm diameter;

Stem color: Between RHS 148D and RHS 146D;

Stem scales: At stem nodes; lanceolate; emarginate to retuse apex with sharply pointed sides; truncate clasping base; margin entire; dehiscing to leave behind thin scar on stem; about 22 mm wide at base, 16 mm wide in center, and about 35 mm long;

Stem scale color: Between RHS 146B and RHS 148C before dehiscing;

Internodes: Up to 21 cm apart between lowest branches, average about 9.3 cm;

Internode color: Between RHS 138B and RHS 146C;

Foliage: Alternate; ternate to palmately compound with three leaflets; outer two leaflets independent, at nearly 90-degree angle to middle leaflet; up to 6.6 cm long and 10.7 cm wide;

Leaflet: Three; oblanceolate; apex acute; base cuneate; margins entire; petiolate; adaxial and abaxial surfaces matte, glabrous, slightly glaucous adaxial and abaxial; middle lobe to about 6.6 cm long and 1.6 cm wide, side lobes about 6.2 cm long and 1.7 cm wide;

Leaflet color: Newly expanding adaxial nearest RHS 146B, abaxial between RHS 146B and RHS 146C; mature adaxial between RHS 137C and RHS 138A, abaxial between RHS 137C and RHS 138A;

Venation: Pinnate, glabrous, thin, not conspicuous adaxial;

Vein color: Expanding foliage adaxial midrib nearest RHS 146D and secondary veins nearest RHS 146D, abaxial expanding foliage midrib between RHS 145A and RHS 146C and secondary veins nearest RHS 146C; mature adaxial midrib nearest RHS 147C and secondary veins between RHS 137C and RHS 138A, abaxial midrib nearest RHS 146D and secondary veins nearest RHS 137A abaxial;

Petioles: Glabrous; slightly glaucous; concavo-convex; to about 15 mm long and 2 mm wide at base, average about 8 cm long and 1.5 mm wide;

Petiole color: Adaxial center between RHS 147C and 146D and edges RHS 138A, abaxial between RHS 138A and RHS 146C;

Stipules: Narrowly lanceolate, acute apex with base truncate; to about 22 mm long and 8 mm wide, average 20 mm long and 6 mm wide with largest stipules below primary branches and decreasing distally and on secondary branches;

Stipule color: Nearest RHS 138A both surfaces;

Peduncle: Cylindrical with vertical shallow ridges and furrows; glaucous; glabrous; from first flower to apex to about 57 cm long; diameter at the base of first flower to about 5 mm and about 2 mm diameter at the apex;

Peduncle color: Between RHS 145A and RHS 146D in the flowering portions;

Pedicel: Cylindrical, glabrous, glaucous; about 6 mm long and 2 mm diameter;

Pedicel color: Between RHS 148C and RHS 138B;

Calyx: Campanulate; five-lobed; to about 9 mm long, 8 mm tall, and 7 mm across at apex;

Sepals: Five; two dorsal, one ventral, and two lateral; acute apices; entire margins; fused base; dorsal sepals divided about 0.3 mm between each other, and divided about 3 mm between lateral sepals; glabrous adaxial and abaxial; slightly glaucous abaxial and matte adaxial; dorsal sepals to about 9 mm long and 1 mm wide at fusion; lateral and ventral sepals to about 9 mm long and 3 mm across at fusion;

Sepal color: Adaxial nearest RHS 144A; abaxial between RHS 148C and RHS 138B;

Buds one day prior to anthesis: Oblong-elliptic, slightly flatted vertically; to about 25 mm long and 10 mm tall, and 7 mm wide, slightly smaller in distal flowers;

Bud color: One day prior to opening exposed keel petal nearest RHS 1C, enfolded banner petal between RHS 4D and RHS 4C distally mottled nearest RHS 79C, exposed alae petals dorsally between RHS 79A and RHS 79B, and ventrally between RHS 4D and RHS 4C;

Flower: Zygomorphic; papilionaceous; non-secund; held at about 45-degree angle above horizontal; to about 50 flowers per center panicle stem and about 21 per secondary branch; individually to about 24 mm long, 15 mm tall and 15 mm wide at largest portions; consisting of an upper banner, a lower keel made up of two lobes folded around gynoecium and androecium; and two lateral wings or alae laterally appressed against keel;

Flowering season: Seasonally effective for about 3 weeks beginning in late May in Zeeland, MI;

Flower lasting: Remain effective and on raceme for about four days;

Flower fragrance: None detected;

Petals: Five; with a lower fused keel, an upper banner, and two lateral wings or alae; keel comprised of two sections that are folded around stamens and pistil;

*Banner petal*.—Concavo-convex, reflexed upward and backward and slightly pinched in the middle; apex retuse, with rounded emarginate apex notched about 2 mm deep; base claw-like, margin entire; to about 20 mm long, 23 mm across natural width, 24 mm wide flattened spread and 6 mm deep; basal portion attenuate claw-like, 4 mm long and 2 mm wide at base.

*Banner color*.—Adaxial 5 mm of margin nearest RHS 155B, an inside ring about 4 mm wide heavily blushed to solid nearest RHS 90B, center 5 mm wide eye nearest RHS 11D, and claw and midrib nearest RHS 145D; abaxial 5 mm or margin nearest RHS 155B, inside ring about 5 mm wide heavily blushed to solid nearest 90B, center 5 mm wide eye nearest 155D, claw nearest RHS 145D, and midrib nearest RHS 1488B.

*Keel*.—Comprised of two separate petals that are wrapped around stamens and pistil; rounded apices; bases separate and claw-like with a small basal lobe about 2 mm long and 2 mm wide above each claw pointing toward base; margin entire; each main lobe about 19 mm long and 8 mm across in middle; blade portion to about 17 mm long and 8 mm tall; with claw to about 6 mm long and base narrowed to 1.5 mm wide in the proximal 2 mm.

*Keel color*.—Adaxial and abaxial claw nearest RHS 145D; adaxial and abaxial distally nearest RHS 4D, adaxial and abaxial proximally with basal lobe nearest RHS 155A.

*Alae*.—Two; papilionaceous corolla appendage with rounded apex, entire margin, claw-like and auriculate base having two small lobes 2 mm long by 2 mm wide pointing toward base; blade about 19 mm long and 12 mm wide near center, with the claw 6 mm long, 2 mm wide at base of blade, and 1.5 mm wide at base.

*Alae color*.—Adaxial and abaxial claw nearest RHS 157D; adaxial lobe center solid transitioning to moderately blushed toward margins to nearest RHS 90A, and margins and basal lobes nearest RHS 155B; abaxial center nearest RHS, margins nearest RHS 155B and basal lobes nearest RHS 3D. Colors not changing significantly with maturity.

Receptacle: Disk-shaped, about 3.5 mm diameter and 2 mm depth;

Receptacle color: Nearest RHS 147C;

Gynoecium: One, with superior ovary and stipe; to about 20 mm long;

*Style*.—Cylindrical; glabrous; slightly lustrous; tapered and arcuate upwards near stigma, about 12 mm long and about 0.7 mm diameter above ovary; color nearest RHS 145B.

*Stigma*.—About 0.2 mm diameter; color nearest RHS 145B.

*Ovary*.—Superior above hypanthium; suspended by stipe; about 8 mm long and about 2 mm in diameter; color nearest RHS 143A.

*Stipe*.—Cylindrical; glabrous; slightly lustrous; about 4 mm long and 0.7 mm diameter; color nearest RHS 143A.

Androecium:

*Stamens*.—Ten.

*Filament*.—Glabrous; slightly lustrous; not united; to 24 mm in length and about 1 mm in diameter; slightly arcuate upward distally; color nearest RHS 145D.

*Anther*.—Dorsifixed; longitudinal; slightly flattened ellipsoid; about 2 mm long and 1.5 mm wide; color nearest RHS 17A.

*Pollen*.—Spherical; abundant; color nearest RHS 17A.

Fruit and seed have not be observed under the present growing condition;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed.

It is claimed:

1. A new and distinct cultivar of *Baptisia* plant named 'Musical Duet' as herein described and illustrated.

* * * * *